(12) United States Patent
Turner et al.

(10) Patent No.: US 10,426,199 B2
(45) Date of Patent: Oct. 1, 2019

(54) CARTRIDGE, COMPONENTS AND METHODS FOR GENERATING AN INHALABLE MEDIUM

(71) Applicant: BRITISH AMERICAN TOBACCO (INVESTMENTS) LIMITED, London (GB)

(72) Inventors: Dominic Turner, London (GB); Colin Dickens, London (GB)

(73) Assignee: BRITISH AMERICAN TOBACCO (INVESTMENTS) LIMITED, London (GB)

( * ) Notice: Subject to any disclaimer, the term of this patent is extended or adjusted under 35 U.S.C. 154(b) by 16 days.

(21) Appl. No.: 15/553,742

(22) PCT Filed: Feb. 26, 2016

(86) PCT No.: PCT/EP2016/054159
§ 371 (c)(1),
(2) Date: Aug. 25, 2017

(87) PCT Pub. No.: WO2016/135331
PCT Pub. Date: Sep. 1, 2016

(65) Prior Publication Data
US 2018/0035719 A1 Feb. 8, 2018

(30) Foreign Application Priority Data

Feb. 27, 2015 (GB) .................................. 1503411.9
Mar. 20, 2015 (GB) .................................. 1504756.6

(51) Int. Cl.
*A24F 13/00* (2006.01)
*A24F 17/00* (2006.01)
(Continued)

(52) U.S. Cl.
CPC ......... *A24F 47/008* (2013.01); *A61M 11/042* (2014.02); *A61M 15/06* (2013.01); *A61M 15/0001* (2014.02); *A61M 16/105* (2013.01)

(58) Field of Classification Search
CPC ....... A61M 11/04; A61M 5/06; A24F 47/008; A24F 47/002
(Continued)

(56) References Cited

U.S. PATENT DOCUMENTS 4,756,318 A 7/1988 Clearman
4,913,169 A 4/1990 Templeton
(Continued)

FOREIGN PATENT DOCUMENTS

AT 507187 A4 3/2010
CA 885796 11/1971
(Continued)

OTHER PUBLICATIONS

International Preliminary Report on Patentability, International Application No. PCT/EP2016/054159, dated Jul. 14, 2017, 7 pages.
(Continued)

*Primary Examiner* — Hae Moon Hyeon
(74) *Attorney, Agent, or Firm* — Patterson Thuente Pedersen, P.A.

(57) ABSTRACT

A cartridge is provided for use with an apparatus for generating an inhalable medium. The cartridge has a container for holding a liquid and a receptacle for receiving a solid material. A shell is provided around the outside of the liquid container. A channel is defined between the liquid container and the shell. Liquid exiting the container can flow, in the form of at least one of a vapor and an aerosol, through the channel to the receptacle and through solid material received by the receptacle in use.

23 Claims, 7 Drawing Sheets

(51) Int. Cl.
*A24F 25/00* (2006.01)
*A24F 47/00* (2006.01)
*A61M 11/04* (2006.01)
*A61M 15/06* (2006.01)
*A61M 15/00* (2006.01)
*A61M 16/10* (2006.01)

(58) Field of Classification Search
USPC .................................. 131/329, 328, 222, 180
See application file for complete search history.

(56) References Cited

U.S. PATENT DOCUMENTS

| | | | |
|---|---|---|---|
| 5,027,836 A | 7/1991 | Shannon | |
| 5,115,820 A | 5/1992 | Hauser | |
| 5,327,915 A | 7/1994 | Porenski | |
| 5,820,967 A | 10/1998 | Gadkaree | |
| 6,814,786 B1 | 11/2004 | Zhuang | |
| 7,160,366 B2 | 1/2007 | Blackburn | |
| 8,997,753 B2 | 4/2015 | Li | |
| 9,259,031 B2 | 2/2016 | Branton | |
| D761,998 S | 7/2016 | Pinder | |
| D768,915 S | 10/2016 | Wright | |
| D782,728 S | 3/2017 | Pinder | |
| D782,729 S | 3/2017 | Wright | |
| D805,684 S | 12/2017 | Thuery | |
| D815,342 S | 4/2018 | Sutton | |
| D818,635 S | 5/2018 | Pinder | |
| D818,638 S | 5/2018 | Wright | |
| D825,099 S | 8/2018 | Wright | |
| D825,103 S | 8/2018 | Wright | |
| 2004/0194792 A1 | 10/2004 | Zhuang | |
| 2005/0133051 A1 | 6/2005 | Luan | |
| 2005/0133054 A1 | 6/2005 | Fournier | |
| 2006/0144412 A1 | 7/2006 | Mishra | |
| 2006/0201524 A1 | 9/2006 | Zhang | |
| 2007/0023056 A1 | 2/2007 | Cantrell | |
| 2007/0215168 A1 | 9/2007 | Banerjee | |
| 2008/0092912 A1* | 4/2008 | Robinson | A24F 47/008 131/200 |
| 2008/0110470 A1 | 5/2008 | Zhang | |
| 2011/0088707 A1 | 4/2011 | Hajaligol | |
| 2011/0226236 A1 | 9/2011 | Buchberger | |
| 2012/0042885 A1 | 2/2012 | Stone | |
| 2012/0318882 A1 | 12/2012 | Abehasera | |
| 2013/0133675 A1 | 5/2013 | Shinozaki | |
| 2013/0192620 A1 | 8/2013 | Tucker | |
| 2014/0048085 A1 | 2/2014 | Cox | |
| 2014/0166029 A1 | 6/2014 | Weigensberg | |
| 2014/0261486 A1* | 9/2014 | Potter | A24F 47/008 131/328 |
| 2014/0299125 A1 | 10/2014 | Buchberger | |
| 2014/0305449 A1 | 10/2014 | Plojoux | |
| 2014/0356607 A1 | 12/2014 | Woodcock | |
| 2015/0027454 A1* | 1/2015 | Li | A24F 47/008 131/328 |
| 2015/0196059 A1* | 7/2015 | Liu | A24F 47/008 131/329 |
| 2015/0257447 A1* | 9/2015 | Sullivan | A24F 47/008 131/329 |
| 2016/0120224 A1* | 5/2016 | Mishra | A24F 47/008 392/390 |
| 2016/0174610 A1* | 6/2016 | Kuczaj | A24F 47/008 131/328 |
| 2016/0255879 A1 | 9/2016 | Paprocki | |
| 2017/0042221 A1 | 2/2017 | England | |
| 2017/0143038 A1 | 5/2017 | Dickens | |
| 2018/0027882 A1* | 2/2018 | Hepworth | A61M 15/06 |
| 2018/0360122 A1 | 12/2018 | Aoun | |

FOREIGN PATENT DOCUMENTS

| | | |
|---|---|---|
| CA | 2330782 | 7/2002 |
| CA | 2925645 A1 | 4/2015 |
| CN | 1054887 | 10/1991 |
| CN | 101433818 | 5/2009 |
| CN | 101557728 | 10/2009 |
| CN | 102834027 | 12/2012 |
| CN | 103315402 A | 9/2013 |
| CN | 103892467 | 7/2014 |
| CN | 204273243 U | 4/2015 |
| DE | 2940535 | 10/1980 |
| EP | 0 174 645 A2 | 3/1986 |
| EP | 0254551 | 1/1988 |
| EP | 0 307 118 | 8/1988 |
| EP | 0 352 106 A2 | 1/1990 |
| EP | 0 535 695 A2 | 4/1993 |
| EP | 0585016 | 3/1994 |
| EP | 845220 | 6/1998 |
| EP | 2489391 A1 | 8/2012 |
| EP | 3127443 | 2/2017 |
| JP | 06064983 | 3/1994 |
| JP | 2009191148 | 8/2009 |
| JP | 2012506263 | 3/2012 |
| JP | 2014 529996 A | 11/2014 |
| JP | 2015504667 | 2/2015 |
| KR | 20120053521 | 5/2012 |
| KR | 20140118982 | 10/2014 |
| WO | WO 98/28994 | 12/1997 |
| WO | WO 9748293 | 11/1998 |
| WO | WO 9748296 | 11/1998 |
| WO | WO 2001030184 | 5/2001 |
| WO | WO 03008068 | 1/2003 |
| WO | WO 03/034847 A1 | 5/2003 |
| WO | WO2004086888 | 10/2004 |
| WO | WO 2004087309 | 10/2004 |
| WO | WO 2006048766 | 5/2006 |
| WO | WO 2006070291 | 7/2006 |
| WO | WO 2006072889 | 7/2006 |
| WO | WO 2006089404 | 8/2006 |
| WO | WO 2006097852 | 9/2006 |
| WO | WO 2006103404 | 10/2006 |
| WO | WO 2006109189 | 10/2006 |
| WO | WO 2007031876 | 3/2007 |
| WO | WO 2007036814 | 4/2007 |
| WO | WO 2007069093 | 6/2007 |
| WO | WO 2013034458 | 3/2013 |
| WO | WO 2013/102309 | 7/2013 |
| WO | WO 2014/116974 A1 | 7/2014 |
| WO | WO 2015/046385 A1 | 4/2015 |
| WO | WO 2015/128499 A1 | 9/2015 |
| WO | WO 2015/179388 A1 | 11/2015 |
| WO | WO 2016/062777 A1 | 4/2016 |

OTHER PUBLICATIONS

International Search Report, International Application No. PCT/EP2016/054159, dated Jun. 9, 2016, 3 pages.
Application and File History for U.S. Appl. No. 15/307,074, filed Oct. 27, 2016, Inventor: England.
Application and File History for U.S. Appl. No. 14/124,637, filed Feb. 7, 2014, Inventor Branton.
Definition of "throughout," the Free Merriam-Webster Dictionary, retrieved from the Internet on Mar. 7, 2015, available at: http://www.merriam-webster.com/dictionary/throughout.
International Search Report and Written Opinion, dated Sep. 17, 2012 for PCT/GB2012/051257, filed Jun. 1, 2012, 7 pages . . . .
Written Opinion of the IPEA, dated May 29, 2013 for PCT/GB2012/051257, filed Jun. 1, 2012.
International Preliminary Report on Patentability, dated Jul. 12, 2013 for PCT/GB2012/051257, filed Jun. 1, 2012, 20 pages.
Australian Examination Report, Application No. 2015334902, dated May 11, 2018, 3 pages.
Canadian Office Action, Application No. 2,963,957, dated Mar. 16, 2018, 4 pages.
Korean Office Action, Application No. 10-2017-7013874, dated Apr. 25, 2018, 7 pages (14 pages with translation).
Application and Filing Receipt for U.S. Appl. No. 16/058,604, filed Aug. 8, 2018, Inventors: Aoun et al.
Chinese Office Action, Application No. 201580023949.5, dated Jul. 2, 2018, 23 pages.

(56) References Cited

OTHER PUBLICATIONS

Japanese Office Action, Application No. 2017-545245, dated Oct. 30, 2018, 11 pages.
Japanese Office Action, Application No. 2017-545230, dated Nov. 6, 2018, 10 pages.
Korean Office Action, Application No. 10-2017-7013874, dated Oct. 30, 2018, 9 pages (19 pages with translation).
European Communication, Application No. 15793718.6, dated Dec. 20, 2018, 5 pages.
Application and File History for U.S. Appl. No. 15/521,082, filed Apr. 21, 2017, Inventor: Aoun.
International Search Report, Application No. PCT/EP2015/074395, dated Feb. 1, 2016, 2 pages.
Application and File History for U.S. Appl. No. 15/553,785, filed Aug. 25, 2017, Inventor: Hepworth.
JAC Vapour E-Cigarettes & E-Liquids, Round Rubber Mouth Tips, www.jacapour.com , 2 pages. May 29, 2015.
International Preliminary Report on Patentability, International Application No. PCT/EP2016/054232, dated Jul. 3, 2017, 10 pages.
International Search Report, International Application No. PCT/EP2016/054232, dated Aug. 24, 2016, 5 pages.
GB Search Report, Application No. GB1517470.9, dated Mar. 21, 2016, 4 pages.
Partial International Search Report, International Application No. PCT/EP2016/054232, dated Jun. 22, 2016, 6 pages.
Application and File History for U.S. Appl. No. 15/307,074, filed Oct. 27, 2016, Inventor: England, as available on.
Australian Examination Report, Application No. 2015334902, dated Dec. 22, 2017, 3 pages.
Application and File History for U.S. Appl. No. 14/124,637, filed Feb. 7, 2014, Inventor Branton as available on.

\* cited by examiner

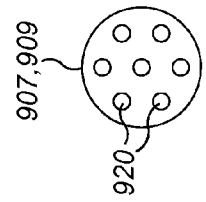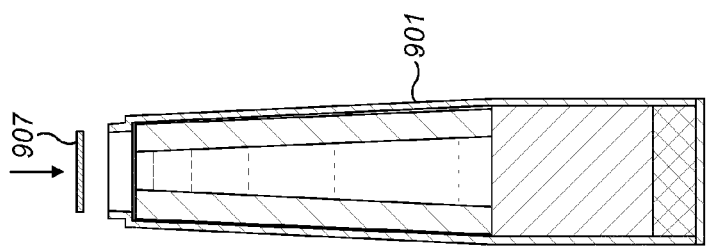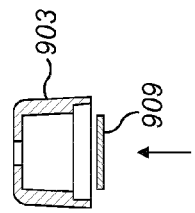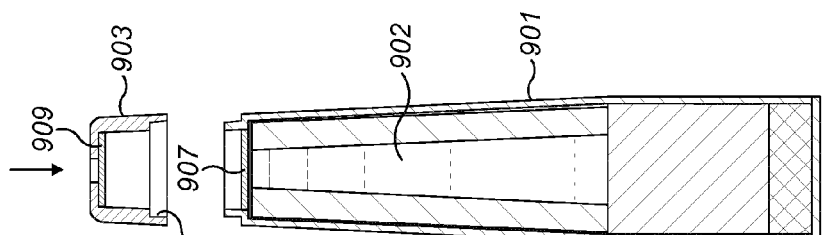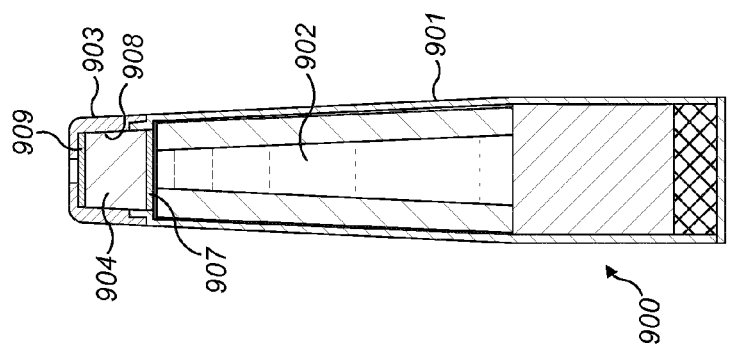

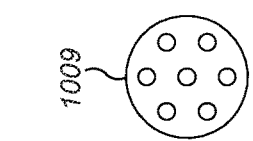
FIG. 10e
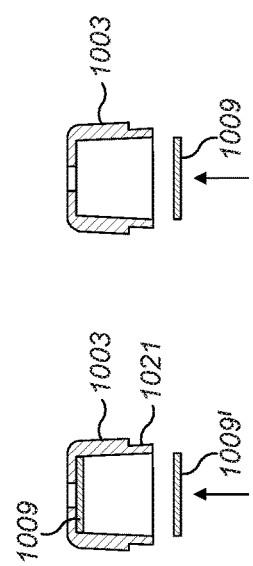
FIG. 10d
FIG. 10c
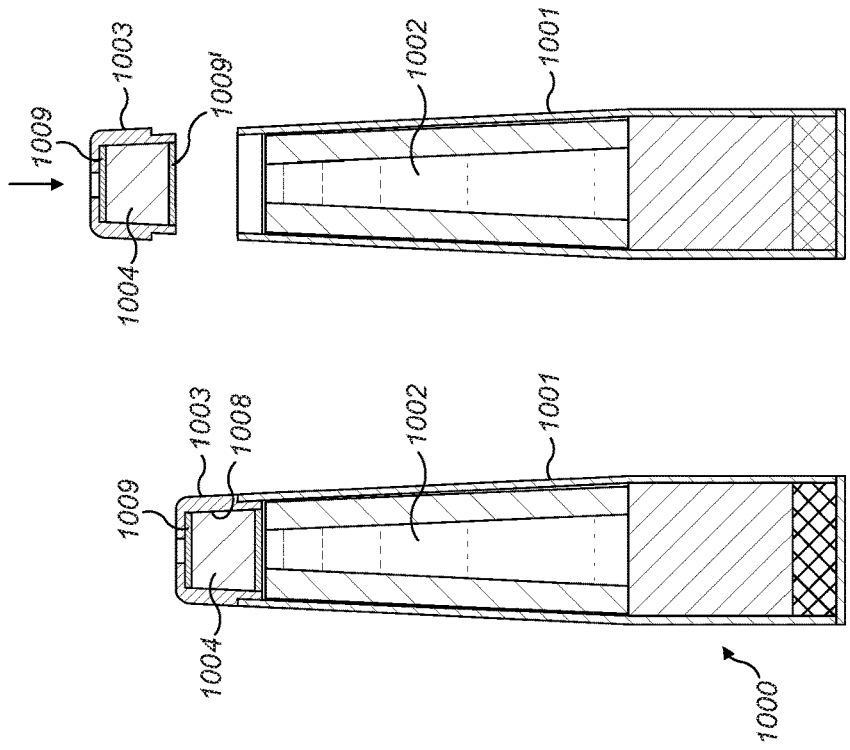
FIG. 10b
FIG. 10a

CARTRIDGE, COMPONENTS AND METHODS FOR GENERATING AN INHALABLE MEDIUM

CROSS-REFERENCE TO RELATED APPLICATIONS

The present application is a National Phase 5 entry of PCT Application No. PCT/EP2016/054159, filed Feb. 26, 2016, which claims priority from GB Patent Application No. 1503411.9, filed Feb. 27, 2015, and GB Patent Application No. 1504756.6, filed Mar. 20, 2015, each of which is hereby fully incorporated herein by reference.

TECHNICAL FIELD

The present disclosure relates to a cartridge for use with an apparatus for generating an inhalable medium, a method of generating an inhalable medium, certain components of a cartridge for use with an apparatus for generating an inhalable medium, and to a method of forming a cartridge.

BACKGROUND

Smoking articles such as cigarettes, cigars and the like burn tobacco during use to create tobacco smoke. Attempts have been made to provide alternatives to these articles that burn tobacco by creating products that release compounds without burning. Examples of such products are heating devices which release compounds by heating, but not burning, the material. The material may be for example tobacco or other non-tobacco products, which may or may not contain nicotine. As another example, there are so-called e-cigarette devices. These devices typically contain a liquid which is heated to vaporize the liquid to produce an inhalable vapor or aerosol. The liquid may contain nicotine and/or flavorings and/or aerosol-generating substances, such as glycerol. The known e-cigarette devices typically do not contain or use tobacco.

SUMMARY

According to a first aspect of the present disclosure, there is provided a cartridge for use with an apparatus for generating an inhalable medium, the cartridge comprising: a container for holding a liquid; a receptacle for receiving a solid material; a shell around the outside of the liquid container; and a channel defined between the liquid container and the shell; the cartridge being arranged such that in use liquid exiting the container can flow, in the form of at least one of a vapor and an aerosol, through the channel to the receptacle and through solid material received by the receptacle in use.

This allows the inhalable medium to have, for example, a flavor or flavors that are derived from the material contained in the receptacle in use. In a particular application, the vapor or aerosol passing over the material is hot and so heats the material to evaporate or volatilize one or more constituents from the material, allowing the constituents to be taken up into the inhalable medium.

As a particular non-limiting example, the material may be or include tobacco. One feature of so-called e-cigarette devices is that the flavor of the inhalable medium is often nothing like or at least is different from the flavor of a conventional tobacco product. In the case that the material in an embodiment of the present disclosure is or includes tobacco, the vapor or aerosol that passes over the tobacco picks up tobacco flavorings from the material.

In an embodiment, the cartridge has a single substantially tubular channel defined between the liquid container and the shell.

In an embodiment, the cartridge has plural channels defined between the liquid container and the shell.

In an embodiment, the channel is an annular channel defined between the liquid container and the shell and substantially surrounding the liquid container.

In an embodiment, the container is frustoconical.

In an embodiment, the cartridge comprises a heater associated with the container for volatilizing a liquid held in the container in use.

In an embodiment, the cartridge comprises a heater associated with the receptacle for heating a solid material received by the receptacle in use. This enables the material to be heated by the heater, which encourages release of compounds from the material, and optionally allows a lower temperature to be used for the heated liquid.

In an embodiment, the container has one or more apertures to allow liquid to exit the container.

In an embodiment, the cartridge comprises a wick for wicking liquid held in the container in use out of the container.

In an embodiment, the container and the receptacle are provided as an integral component.

In an embodiment, the container and the receptacle are provided as separate components which are detachably connected to each other.

In an embodiment, the receptacle has at least one retainer for retaining solid material within the receptacle in use.

In an embodiment, the at least one retainer has at least one through hole through which the vapor or aerosol can pass.

In an embodiment, the retainer is a disk.

In an embodiment, the retainer is an end wall of the receptacle.

In an embodiment, the cartridge comprises a wall between the container and the receptacle, the wall having at least one through hole through which the vapor or aerosol can pass.

In an embodiment, the receptacle has a transparent wall so that the contents of the receptacle are visible.

In an embodiment, the receptacle contains a solid material.

In an embodiment, the solid material is or comprises tobacco.

In an embodiment, the solid material is wrapped in a transparent material.

In an embodiment, the container holds a liquid. In an embodiment, the liquid contains nicotine. In an embodiment, the liquid is or comprises glycerol. In an embodiment, the liquid is or comprises a flavorant.

There may also be provided in combination, a cartridge and an apparatus for generating an inhalable medium, the cartridge being a cartridge as described above, the apparatus having a battery section and a mouthpiece, the cartridge being connectable to the apparatus.

According to a second aspect of the present disclosure, there is provided a method of generating an inhalable medium using a cartridge and an apparatus, wherein the apparatus comprises a battery section and a mouthpiece, and wherein the cartridge comprises a container containing a liquid, a receptacle containing a solid material, a shell around the outside of the liquid container, and a channel defined between the liquid container and the shell, the cartridge being connected to the apparatus, the method comprising: heating liquid drawn from the container to vaporise the liquid; passing the vaporised liquid through the channel defined between the liquid container and the shell of the cartridge, into the receptacle containing the solid material and through the solid material so as to entrain at least flavor from the solid material; and passing the flavored aerosol through the mouthpiece of the apparatus.

According to a third aspect of the present invention, there is provided a receptacle for receiving a solid material, the receptacle being for use with a container for holding a liquid to form a cartridge for use with an apparatus for generating an inhalable medium, the receptacle having a connector to enable the receptacle to be connected to a said container.

In an embodiment, the connector is in the form of an annular end wall that is receivable in or around a said container.

In an embodiment, the receptacle has at least one retainer for retaining solid material within the receptacle in use.

In an embodiment, the at least one retainer has at least one through hole through which the vapor or aerosol can pass.

In an embodiment, the retainer is a disk.

In an embodiment, the retainer is an end wall of the receptacle.

In an embodiment, the receptacle contains a solid material.

In an embodiment, the solid material is or comprises tobacco. The tobacco may for example be cut tobacco, reconstituted tobacco, ground tobacco, etc., and may include different varieties of tobacco.

According to a fourth aspect of the present invention, there is provided a container for holding a liquid, the container being for use with a receptacle for receiving a solid material to form a cartridge for use with an apparatus for generating an inhalable medium, the container having an inner container for holding a liquid, a shell around the outside of the liquid container, and a channel defined between the inner container and the shell, and a connector to enable the container to be connected to a said receptacle.

In an embodiment, the connector is in the form of an annular end wall that is receivable in or around a said receptacle.

In an embodiment, the cartridge has a single substantially tubular channel defined between the inner container and the shell.

In an embodiment, the cartridge has plural channels defined between the inner container and the shell.

In an embodiment, the channel is an annular channel defined between the inner container and the shell and substantially surrounding the inner container.

In an embodiment, the container is frustoconical.

According to a fifth aspect of the present disclosure, there is provided a method of forming a cartridge for use with an apparatus for generating an inhalable medium, the method comprising: loading a container with a liquid; loading a receptacle with solid material; and connecting the container and the receptacle together, such that in use liquid exiting the container can flow, in the form of at least one of a vapor and an aerosol, through solid material received by the receptacle in use.

In an embodiment, the loading the receptacle with solid material comprises cutting a rod of the solid material to a desired length and placing the cut rod of solid material into the receptacle prior to connecting the container and the receptacle together.

In an embodiment, the solid material is wrapped in a transparent material.

In an embodiment, the solid material is or comprises tobacco.

BRIEF DESCRIPTION OF THE DRAWINGS

Embodiments of the disclosure will now be described, by way of example only, with reference to the accompanying drawings, in which:

FIGS. 9a-9e show schematic longitudinal cross-sectional views of an example of a cartridge having a liquid container and a separate container for solid material and components thereof.

FIGS. 10a-10e show schematic longitudinal cross-sectional views of an example of a cartridge having a liquid container and a separate container for solid material and components thereof.

DETAILED DESCRIPTION

Figure 1:
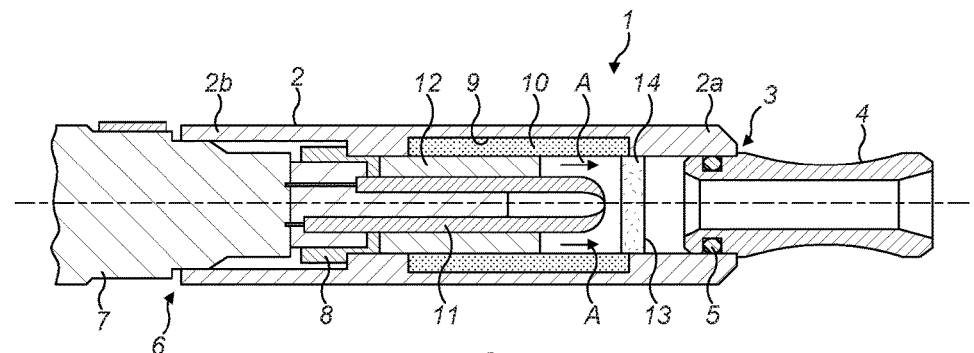
FIG. 1 shows a schematic longitudinal cross-sectional view of an apparatus for generating an inhalable medium.

Referring to FIG. 1, there is shown an example of an apparatus 1 for generating an inhalable medium. In broad outline, the apparatus 1 volatilizes a liquid to form a vapor or an aerosol which passes through a material so as to produce an inhalable medium that contains one or more constituents derived from the material.

In this respect, first it may be noted that, in general, a vapor is a substance in the gas phase at a temperature lower than its critical temperature, which means that for example the vapor can be condensed to a liquid by increasing its pressure without reducing the temperature. On the other hand, in general, an aerosol is a colloid of fine solid particles or liquid droplets, in air or another gas. A "colloid" is a substance in which microscopically dispersed insoluble particles are suspended throughout another substance.

Returning to FIG. 1, the apparatus 1 of this example has a generally hollow cylindrical outer housing 2. The housing 2 has an open end 3. In this example, a tubular mouthpiece 4 is provided in the open end 3. The mouthpiece 4 in this example is removable by a user from the housing 2. An O-ring or other seal 5 assists in sealing the mouthpiece 4 in the housing 2. At or towards the other end 6 of the housing 2 is a battery 7 for powering various components of the apparatus 1, as will be discussed further below. The battery 7 may be a rechargeable battery or a disposable battery. A controller 8 is also provided in the housing 2 for controlling the operation of various components of the apparatus 1, as will be discussed further below.

The housing 2 has a container 9 for holding or containing a liquid 10. Various different forms for the container 9 may be used. In the example of FIG. 1, the container 9 is in the form of an annular chamber 9 provided in the housing 2 between the open end 3 and the other end 6. In this particular example, the housing 2 is in two parts, a first part 2a being towards the open end 3 and a second part 2b towards the other end 6. The first and second parts 2a,2b of the housing 2 may connect to each other via a screw thread, a bayonet fitting or the like. In use, a user can separate the first and second parts 2a,2b of the housing 2 to allow the liquid 10 to be replenished or replaced as necessary. Alternatively, the mouthpiece 4 can be removed to provide access to the container 9. It will be understood however that other arrangements are possible. For example, the liquid 10 may be provided in a discrete annular pot-like container which can be removed as a whole from the housing 2. Such a discrete container may be disposable so that the user replaces the liquid 10 by fitting a new container with liquid 10 in the housing 2.

Alternatively, such a container may be reusable. In such a case, the user may replenish or replace liquid 10 in the container whilst it has been removed from the housing 2 and then replace the refilled container in the housing 2. It will be understood that the housing 2 need not be in two parts and that other arrangements enabling access for the user may be provided, for example, to enable refilling in situ.

A heater 11 is provided generally centrally of the housing 2, that is, centrally along the length and width of the housing 2 in this example. In this example, the heater 11 is powered by the battery 7 and is therefore electrically connected to the battery 7. The heater 11 may be an electrically resistive heater, including for example a nichrome resistive heater, a ceramic heater, etc. The heater 11 may be for example a wire, which may for example be in the form of a coil, a plate (which may be a multi-layer plate of two or more different materials, one or more of which may be electrically conductive and one or more of which may be electrically non-conductive), a mesh (which may be woven or non-woven for example, and which again may be similarly multi-layer), a film heater, etc. Other heating arrangements may be used, including non-electrical heating arrangements.

This heater 11 is provided for volatilizing the liquid 10. In the example shown, an annular wick 12 surrounds the heater 11 and is in (thermal) contact with the heater 11. The outermost surface of the annular wick 12 is in contact with liquid 10 contained in the liquid container 9. The wick 12 is generally absorbent and acts to draw in liquid 10 from the liquid container 9 by capillary action. The wick 12 is preferably non-woven and may be for example a cotton or wool material or the like, or a synthetic material, including for example polyester, nylon, viscose, polypropylene or the like, or a ceramic material. Whilst this will be described more fully below, it may be noted here that in use, liquid 10 drawn into the wick 12 is heated by the heater 11. The liquid 10 may be volatilized so as to produce an aerosol of liquid droplets or sufficiently heated to produce a vapor. The aerosol or vapor so produced exits the wick 12 and passes towards the mouthpiece 4 as shown by the arrows A under the action of the user drawing on the mouthpiece 4. The heater 11 and wick 12 may be provided as a single, effectively integral item such that the heating and wicking is effectively carried out by a single unit.

The housing 2 further contains a chamber or receptacle 13 which holds or contains a material 14 in the apparatus 1. In use, a user can access the chamber or receptacle 13 to replace or replenish the material 14 through the open end 3 of the housing 2 by removing the mouthpiece 4 and/or by separating the two parts 2a,2b of the housing 2. Various different forms for the chamber or receptacle 13 may be used. For example, the chamber or receptacle 13 may be a tube which is completely open at both ends and which contains the material 14. As another example, the chamber or receptacle 13 may be a tube which has one or more end walls which have through holes through which a vapor or aerosol can pass. The chamber or receptacle 13 may remain in situ within the housing 2 whilst the user removes and replaces the material 14. Alternatively, the chamber or receptacle 13 containing the material may be a discrete item which in use is inserted into and removed from the housing 2 as a whole. A removable chamber or receptacle 13 of this type may be disposable so that the user replaces the material 14 by fitting a new chamber or receptacle 13 containing fresh material 14 into the housing 2. As an alternative, the chamber or receptacle 13 may be reusable. In such a case, the user may replace the material 14 in the chamber or receptacle 13 whilst the chamber or receptacle 13 has been removed from the housing 2 and then replace the refilled chamber or receptacle 13 in the housing 2. In yet another example, the chamber or receptacle 13 may comprise clips or the like provided internally of the housing 2 and which retain the material 14 in position. In some examples, the material 14 could simply fit snugly within the chamber or receptacle 13. As another alternative, the container 9 for containing the liquid 10 may itself be arranged to support or carry the material 14. For example, the container 9 may have one or more clips or a tube or the like for receiving and holding the material 14 in position. Such a dual function container 9/chamber or receptacle 13 for both containing the liquid 10 and receiving the material 14 may be in the form of a cartridge or the like and may be a disposable item or may be re-useable, with the liquid 10 and material 14 being replaced or topped up by the user as required. In some cases, it may be that the user only needs to top up or replace the material 14 from time to time, with sufficient liquid 10 being provided for several uses. Once the liquid 10 has been consumed, the user disposes of the dual function container 9/chamber or receptacle 13 and uses a new one. Likewise, it may be that the user only needs to top up or replace the liquid 10 from time to time, with sufficient material 14 being provided for several uses. Once the material 14 has been consumed, the user disposes of the dual function container 9/chamber or receptacle 13 and uses a new one. Specific examples of dual function containers/receptacles are discussed further below.

The material 14 is located in the housing 2 downstream of the location where the aerosol or vapor is produced from the liquid 10 and upstream of the open end 3 of the housing 2 and the mouthpiece 4. In this particular example, the material 14 is effectively provided in the same portion or chamber of the housing 2 as the wick 12. The aerosol or vapor produced from the liquid 10 exits the wick 12 and passes as shown by the arrows A towards the material 14 under the action of the user drawing on the mouthpiece 4. In particular embodiments, the material 14 is porous so that the aerosol or vapor passes through the material 14 and then through the open end 3 of the housing 2 and the mouthpiece 4. In some embodiments, the material 14 and/or its chamber or receptacle 13 are arranged so that there is no air gap between the material 14/chamber or receptacle 13 and the interior of the housing 2 so that the aerosol or vapor flows entirely through the material 14.

The liquid 10 can be a liquid that is volatilizable at reasonable temperatures, such as in the range of 100–300° C. or more particularly around 150-250° C., as that helps to keep down the power consumption of the apparatus 1.

Suitable materials include those conventionally used in e-cigarette devices, including for example propylene glycol and glycerol (also known as glycerine).

The material 14 is a material that may be used to impart a flavor to the aerosol or vapor produced from the liquid 10 as the aerosol or vapor passes through the material 14. The material 14 may for example consist of or comprise tobacco. As the aerosol or vapor passes through and over the tobacco material 14, the hot aerosol or vapor entrains organic and other compounds or constituents from the tobacco material 14 that lend tobacco its organoleptic properties, thus imparting the flavor to the aerosol or vapor as it passes to the mouthpiece 4. It will be understood however that materials other than tobacco may be used to impart different flavors to the aerosol or vapor stream. For example, flavorants could be included in the material or in the liquid.

In addition, where the material 14 is or includes tobacco, it may be that the aerosol or vapor stream draws sufficient nicotine from the tobacco material 14. Alternatively or additionally, where the material 14 does not contain any tobacco, the material 14 may be enhanced with nicotine, for example by coating the material with nicotine. Indeed, even in the case that the material 14 is or includes tobacco, the material 14 may be coated or otherwise enhanced with nicotine. As another example, whether or not the material 14 is or includes tobacco and/or includes nicotine, nicotine may be provided in the liquid 10. Accordingly, where it is intended that the apparatus 1 provides nicotine for the user, the nicotine may be provided in the liquid 10, may be obtained from the material 14 in the case that the material is or includes tobacco, may be provided as a coating or the like on non-tobacco material 14, may be provided as a coating or the like on tobacco material, or any combination of these. Likewise, flavorings may be added to the material 14 (whether or not the material is or includes tobacco) and/or to the liquid 10.

As mentioned above, heating devices are known that release compounds by heating, but not burning, tobacco. It may be noted here that tobacco is a poor heat conductor, and yet the heating of tobacco in known tobacco heating devices is by heat conduction through the tobacco from an exterior surface of the tobacco (typically by virtue of an electrical resistive heating element which is in contact with the surface of the tobacco). This means that the tobacco may be heated inefficiently and/or the power consumption of the device is high. In the case of a battery-operated device, high power consumption is a problem for the user as the battery or batteries need to be recharged or replaced frequently. In the case that the material 14 is tobacco, this can be avoided in embodiments of the present apparatus 1 as the material 14 can be heated by the hot aerosol or vapor passing through the body of the porous tobacco material 14, providing for more effective and efficient heating throughout the body of the tobacco material 14. This can help to lower the power consumption of the apparatus 1.

In the example shown in FIG. 1, the only heat source for heating the material 14 in the apparatus 1, which is required so as to generate the organic and other compounds or constituents from the material 14, is the hot aerosol or vapor produced from heating the liquid 10.

Figure 2:
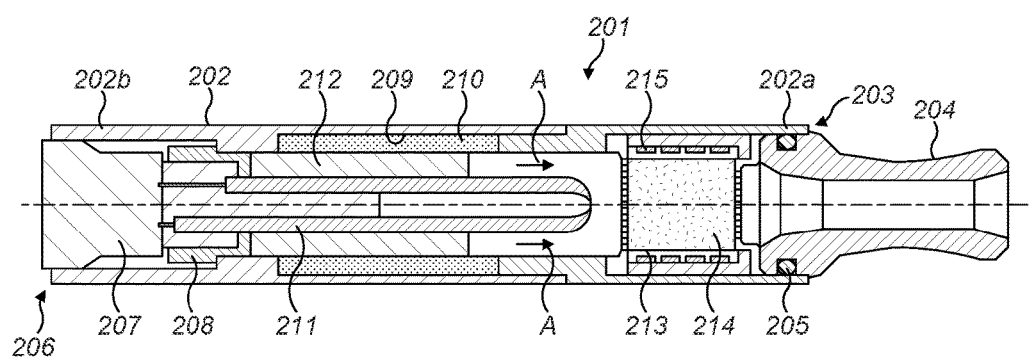
FIG. 2 shows a schematic longitudinal cross-sectional view of another apparatus for generating an inhalable medium.

Referring now to FIG. 2, there is shown another example of an apparatus for generating an inhalable medium. In the following description and in FIG. 2, components and features that are the same as or similar to the corresponding components and features of the example described with reference to FIG. 1 have the same reference numeral but increased by 200. For the sake of brevity, the description of those components and features will not be repeated in its entirety here. It will be understood that the arrangements and alternatives, etc. described above in relation to the example of FIG. 1 are also applicable to the example of FIG. 2. Again, in broad outline, the apparatus 201 of FIG. 2 heats a liquid to form a vapor or an aerosol which passes through a material 214 so as to produce an inhalable medium that contains one or more constituents derived from the material 214.

In the example apparatus 201 of FIG. 2, a second heater 215, such as an oven heater, is provided in thermal contact with the material 214 to pre-heat the material 214 and/or provide additional heat to the material 214 throughout use of the apparatus 201. This encourages release of constituents from the material 214 as the vapor or aerosol passes through the material 214 in use. This also optionally allows a lower temperature to be used for the heated liquid 210, which reduces the power consumption of the first heater 211 which heats the liquid 210, and also may allow the amount of heated liquid 210 that has to be used to achieve sufficient heating of the material 214 to be reduced. The second heater 215 may be an electrically resistive heater, a ceramic heater, etc., powered by for example the battery 207. The second heater 215 may be for example a wire, which may for example be in the form of a coil, a plate (which may be a multi-layer plate of two or more different materials, one or more of which may be electrically conductive and one or more of which may be electrically non-conductive), a mesh (which may be woven or non-woven for example, and which again may be similarly multi-layer), a film heater, etc. Other heating arrangements may be used for the second heater 215, including non-electrical heating arrangements.

In the example apparatus 201 of FIG. 2, the second heater 215 for heating the material 214 is provided externally of the material 214 and heats the material 214 by heat conduction from the exterior of the material 214. The second heater 215 in this example is generally cylindrical. The second heater 215 may in effect be an integral part of the apparatus 201 and be provided as part of the housing 202. As an alternative, the second heater 215 may be provided integrally with the chamber 213 which holds or contains the material 214. In this alternative, in the case that the chamber 213 is disposable, the second heater 215 will be replaced when a new chamber 213 with fresh material is loaded into the apparatus 201 by the user.

Figure 3:
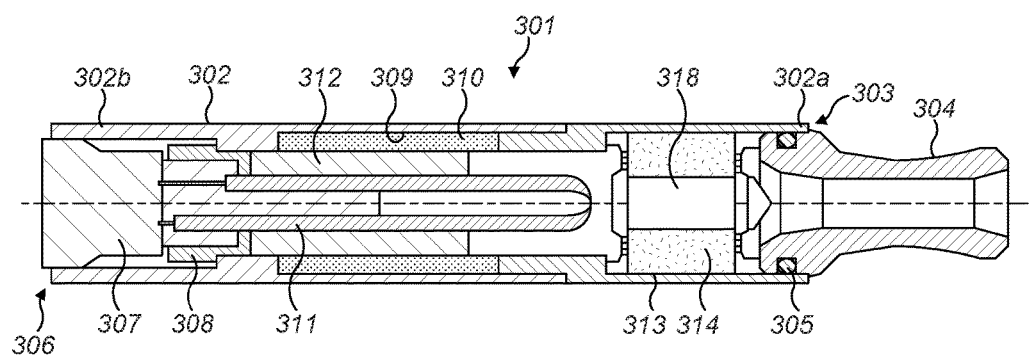
FIG. 3 shows a schematic longitudinal cross-sectional view of another apparatus for generating an inhalable medium.

Referring now to FIG. 3, there is shown another example of an apparatus for generating an inhalable medium. In the following description and in FIG. 3, components and features that are the same as or similar to the corresponding components and features of the example described with reference to FIG. 1 have the same reference numeral but increased by 300. For the sake of brevity, the description of those components and features will not be repeated in its entirety here. It will be understood that the arrangements and alternatives, etc. described above in relation to the examples of FIG. 1 and FIG. 2 are also applicable to the example of FIG. 3. Again, in broad outline, the apparatus 301 of FIG. 3 heats a liquid to form a vapor or an aerosol which passes through a material 314 so as to produce an inhalable medium that contains one or more constituents derived from the material 314.

In the example apparatus 301 of FIG. 3, a second heater 318 is again provided in thermal contact with the material 314 to heat the material 314 to encourage release of constituents from the material 314 as the vapor or aerosol passes through the material 314 in use. The second heater 318 may be an electrically resistive heater, a ceramic heater, etc., powered by for example the battery 307. Other heating arrangements may be used for the second heater 318, including non-electrical heating arrangements.

In the example apparatus 301 of FIG. 3, the second heater 318 for heating the material 314 is provided internally of the material 314 and heats the material 314 by heat conduction from the interior of the material 314. The second heater 318 in this example is generally in the form of a cylindrical rod located along the central longitudinal axis of the material 314. In other arrangements, the second heater 318 may be a wire, which may for example be in the form of a coil, a plate (which may be a multi-layer plate of two or more different materials, one or more of which may be electrically conductive and one or more of which may be electrically non-conductive), a mesh (which may be woven or non-woven for example, and which again may be similarly multi-layer), a film heater, etc. The material 314 in this case is generally tubular or otherwise has an internal aperture for receiving the second heater 318. The second heater 318 may in effect be an integral part of the apparatus 301 and be provided as part of the housing 302. In this case, as the material 314 is loaded into the apparatus 301 (for example, as the chamber 313 containing the material 314 is loaded into the apparatus 301), the material 314 surrounds the second heater 318. As an alternative, the second heater 318 may be provided integrally with the chamber 313 which holds or contains the material 314. In this alternative, in the case that the chamber 313 is disposable, the second heater 318 will be replaced when a new chamber 313 with fresh material is loaded into the apparatus 301 by the user.

In another example, plural internal heaters 318 may be provided, so as to provide for more efficient heating of the material 314. In another example, the material 314 may be heated by both one or more external heaters (like the second heater 215 of the example of FIG. 2) and by one or more internal heaters 314 (like the second heater 318 of the example of FIG. 3).

The apparatus of FIGS. 1-3, and further examples, are described more fully in our International Patent Application No. PCT/EP2015/074395, the entire content of which is hereby incorporated by reference.

Figure 4:
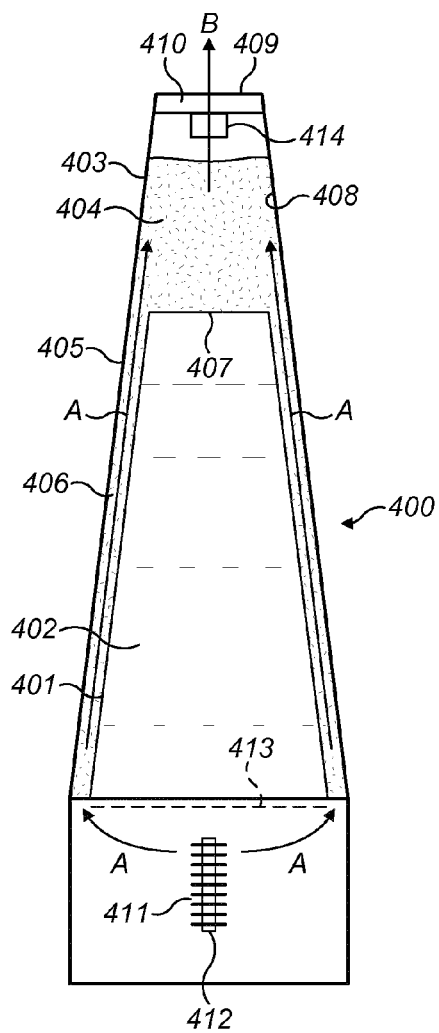
FIG. 4 shows a schematic longitudinal cross-sectional view of an example of a cartridge having a liquid container and an integral container for solid material.

Referring now to FIG. 4, there is shown a schematic longitudinal cross-sectional view of an example of a cartridge 400 having a liquid container 401 for containing liquid 402 and a receptacle or container 403 for material 404, which will typically be solid material 404. In this example, the liquid container 401 and the receptacle or container 403 are provided as one integral component, either by being formed integrally initially or being formed initially of two parts which are then assembled in a substantially permanent fashion. In the case that the liquid container 401 and the receptacle or container 403 are formed initially of two parts, the liquid container 401 and the receptacle or container 403 may be fixed to each other by for example friction welding, such as spin welding, ultrasonic welding, etc. The cartridge 400 is arranged so that as the liquid 402 is volatilized so as to produce an aerosol of liquid droplets or sufficiently heated to produce a vapor, at least some and at least in some embodiments all or substantially all of the aerosol or vapor passes through the material 404 to pick up flavor from the material 404.

In the example of FIG. 4, the liquid container 401 is provided generally centrally of the cartridge 400. The liquid container 401 in the example shown is frustoconical in shape, but may have a different shape, such as conical, cylindrical, etc. The liquid container 401 is surrounded by an outer shell 405 which defines an annular channel 406 around the outside of the length of the liquid container 401 and which extends from one end of the liquid container 401 to the other. The outer shell 405 extends beyond a first end wall 407 of the liquid container 401 to define a chamber 408 beyond the first end wall 407 of the liquid container 401. In the example shown, both the chamber 408 and the annular channel 406 contain the material 404 and so can be regarded as together providing the receptacle or container 403 for the material 404. In other examples, the material 404 may be provided only in the chamber 408, which therefore defines the receptacle or container 403 for the material 404, and the annular channel 406 is empty. The chamber 408 is closed off by an end wall 409 which is spaced from the end wall 407 of the liquid container 401. The end wall 409 may be part of the outer shell 405 or may be a separate plastics or rubber cap or the like. In yet other examples, the annular channel 406 contains the material 404 and there is no material in the chamber 408, and indeed the chamber 408 may be omitted and the annular channel 406 effectively terminates at the end wall 409. The annular channel 406 and/or chamber 408 may be entirely filled with material 404 or may only contain a portion or plug of solid material 404. The end wall 409 is porous and/or has one or more through holes 410 to enable the aerosol or vapor to exit the cartridge 400 to be inhaled by a user. The liquid container 401 and the receptacle or container 403 may each be formed of rigid, watertight and airtight materials, such as metal, suitable plastics, etc.

The example cartridge 400 shown in FIG. 4 is provided with a heater 411 and a wick 412 in (thermal) contact with the heater 411. In this example, the heater 411 and the wick 412 are provided as a single unit. In this case, where the cartridge 400 includes a heater 411, such a cartridge is often referred to as a "cartomiser". The orientation of the heater 411 is shown schematically and for example the heater 411 may be a coil having its longitudinal axis perpendicular to the longitudinal axis of the cartridge 400 rather than parallel as shown in FIG. 4.

The wick 412 is in contact with the liquid 402. This may be achieved by for example the wick 412 being inserted through a through hole (not shown) in the second end wall 413 of the liquid container 401. Alternatively or additionally, the second end wall 413 may be a porous member (shown schematically in FIG. 4 by dashed lines) which allows liquid to pass through from the liquid container 401, and the wick 412 may be in contact with the second end wall 413. The second end wall 413 may be for example in the form of a porous ceramic disk. A second end wall 413 of this type helps to regulate the flow of liquid onto the wick 412. The wick 412 is generally absorbent and acts to draw in liquid 402 from the liquid container 401 by capillary action. The wick 412 is preferably non-woven and may be for example a cotton or wool material or the like, or a synthetic material, including for example polyester, nylon, viscose, polypropylene or the like, or a ceramic material.

In use, the cartridge 400 is connected by the user to a battery section of an apparatus to enable the heater 411 to be powered. (An example of such apparatus will be discussed further below.) When the heater 411 is powered (which may be instigated for example by the user operating a button of the overall apparatus or by a puff detector of the overall apparatus, as is known per se), liquid 402 drawn in from the liquid container 401 by the wick 412 is heated by the heater 411 to volatilize or vaporise the liquid. As the user draws on a mouthpiece of the overall apparatus, the vapor or aerosol passes into the annular channel 406 around the outside of the length of the liquid container 401 and into the chamber 408 as shown by the arrows A. The vapor or aerosol picks up flavor from the material 404. In the case that the material 404 contains or includes nicotine, the vapor or aerosol also contains nicotine entrained from the material 404. The vapor or aerosol can then exit the cartridge 400 through the end wall 409 as shown by the arrow B. A one way valve 414 may be provided inside the end wall 409 so that the vapor or aerosol can only exit the cartridge 400 and cannot back-flow to the heater 411 or the electronics of the apparatus as a whole.

Figure 5:
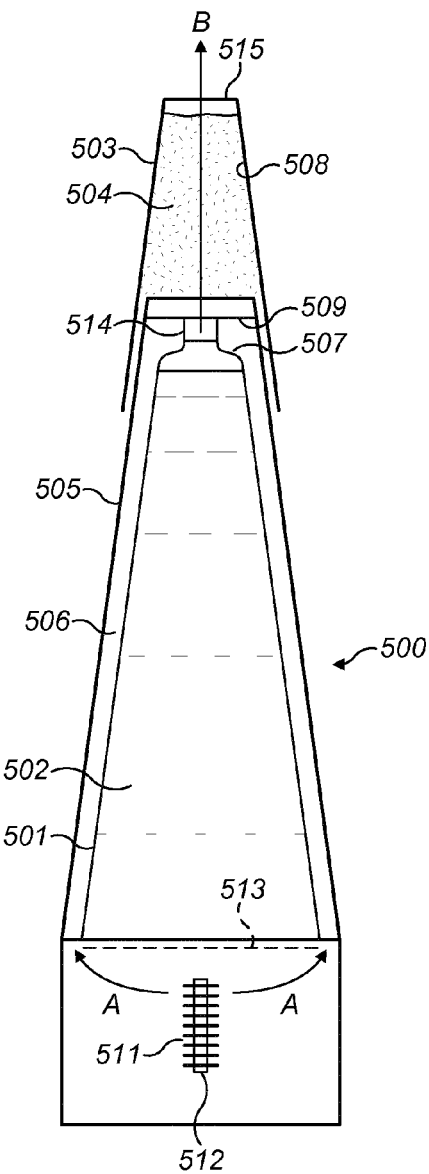
FIG. 5 shows a schematic longitudinal cross-sectional view of an example of a cartridge having a liquid container and a detachable container for solid material.

Referring now to FIG. 5, there is shown a schematic longitudinal cross-sectional view of another example of a cartridge 500 having a liquid container 501 for containing liquid 502 and a container 503 which defines a chamber 508 for containing material 504, which will typically be solid material 504. In the following description and in FIG. 5, components and features that are the same as or similar to the corresponding components and features of the example described with reference to FIG. 4 have the same reference numeral but increased by 100. For the sake of brevity, the description of those components and features will not be repeated in its entirety here.

In this example, the liquid container 501 and the material container 503 of the cartridge 500 are provided as separate components, which are detachably connected to each other in use. The liquid container 501 and the material container 503 may for example be clipped or otherwise detachably fixed to each other, or for example the material container 503 may simply rest on or be a tight friction fit on the liquid container 501. The cartridge 500 is arranged so that as the liquid 502 is volatilized so as to produce an aerosol of liquid droplets or sufficiently heated to produce a vapor, at least some and preferably all or substantially all of the aerosol or vapor passes through the material 504 to pick up flavor from the material 504.

In this example, the liquid container 501 is surrounded by an outer shell 505 which defines an annular channel 506 around the outside of the length of the liquid container 501 and which extends from one end of the liquid container 501 to the other. The outer shell 505 extends beyond a first end wall 507 of the liquid container 501 and terminates in an end wall 509. The end wall 509 may be a separate plastics or rubber cap or the like. The end wall 509 is porous and/or has one or more through holes to enable the aerosol or vapor to exit the annular channel 506. A one way valve 514 may be provided inside the end wall 509 so that the vapor or aerosol can only exit the annular channel 506 at the end remote from the heater 511 and wick 512 and cannot back-flow to the heater 511 or the electronics of the apparatus as a whole. The material container 503 is located in use over the end wall 509 so that vapor or aerosol exiting through the end wall 509 passed into the material container 503. The material container 503 has an exit aperture and/or or a porous end wall 515 to enable the aerosol or vapor to exit the cartridge 500 to be inhaled by a user.

In use, the cartridge 500 is connected by the user to a battery section of an apparatus to enable the heater 511 to be powered. (Again, an example of such apparatus will be discussed further below.) When the heater 511 is powered (which may be instigated for example by the user operating a button of the overall apparatus or by a puff detector of the overall apparatus as is known per se), liquid 502 drawn in from the liquid container 501 through the end wall 513 by the wick 512 is heated by the heater 511 to volatilize or vaporise the liquid. As the user draws on a mouthpiece of the overall apparatus, the vapor or aerosol passes into the annular channel 506 around the outside of the length of the liquid container 501 towards the end wall 509 of the outer shell 505 as shown by the arrows A. The vapor or aerosol then passes through the end wall 509 (via the one-way valve 514 if present) and into the material container 503 where it picks up flavor from the material 504 contained in the material container 503. In the case that the material 504 contains or includes nicotine, the vapor or aerosol also contains nicotine entrained from the material 504. The vapor or aerosol can then exit the cartridge 500 through the end wall 515 of the material container 503 as shown by the arrow B.

Figure 6:
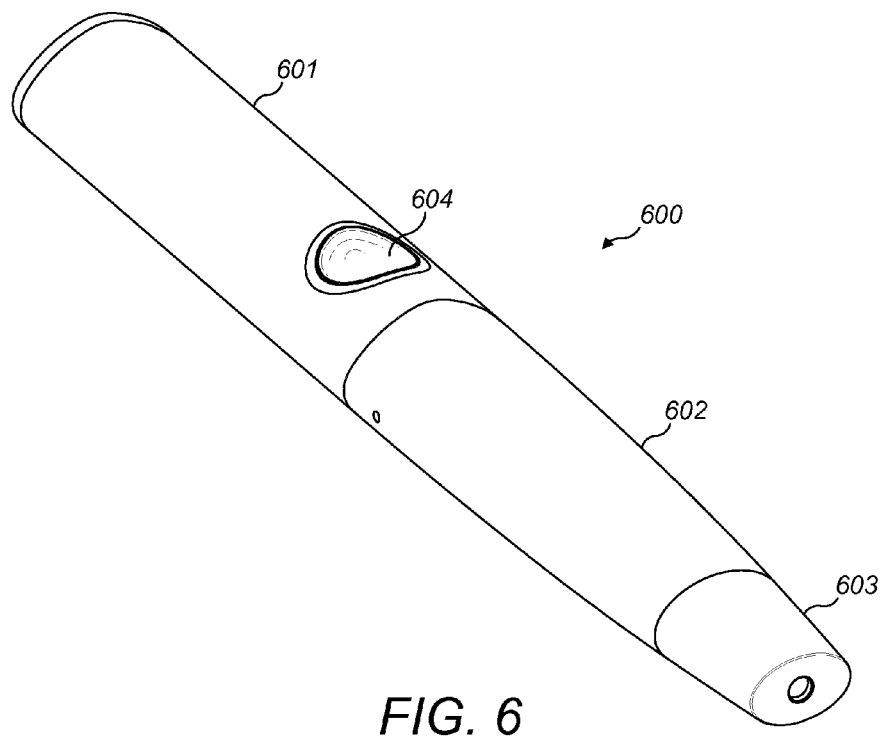
FIGS. 6 and 7 show respectively a perspective view and a side elevation of an example of an apparatus for generating an inhalable medium.
Figure 7:
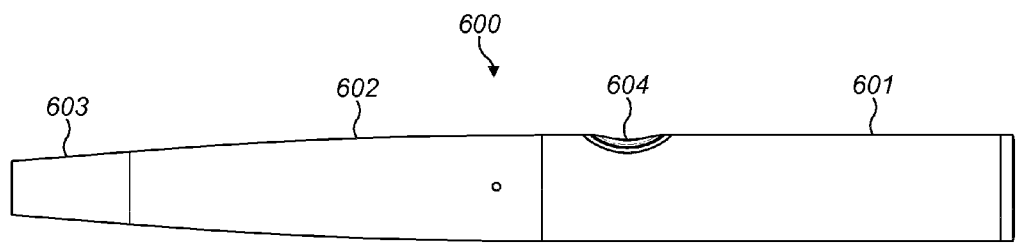

FIGS. 6 and 7 show respectively a perspective view and a side elevation of an example of an apparatus 600 for generating an inhalable medium. The apparatus 600 may be used with any of the cartridges described herein and with other cartridges. The apparatus 600 has a battery section 601 and a cartridge section 602. The battery section 601 and the cartridge section 602 are shown connected to each other in the drawings, but can be separated by a user to allow a cartridge to be loaded into the cartridge section 602. The battery section 601 and the cartridge section 602 can be separably connected to each other using for example a snap-fit connection, clips, a screw thread, etc. The cartridge section 602 has a mouthpiece 603 at its remote end. In this example, the battery section 601 has an on-off or power button 604. The battery section 601 contains a power supply, such as a battery which may be a rechargeable battery or a disposable battery. The battery section 601 also contains a controller for controlling the operation of various components of the apparatus 600 and/or a puff detector. In use, a user separates the battery section 601 and the cartridge section 602, inserts a cartridge into the cartridge section 602, and then connects the battery section 601 and the cartridge section 602 together again. The user can then operate the apparatus 600 using the on-off or power button 604.

Figure 8A:
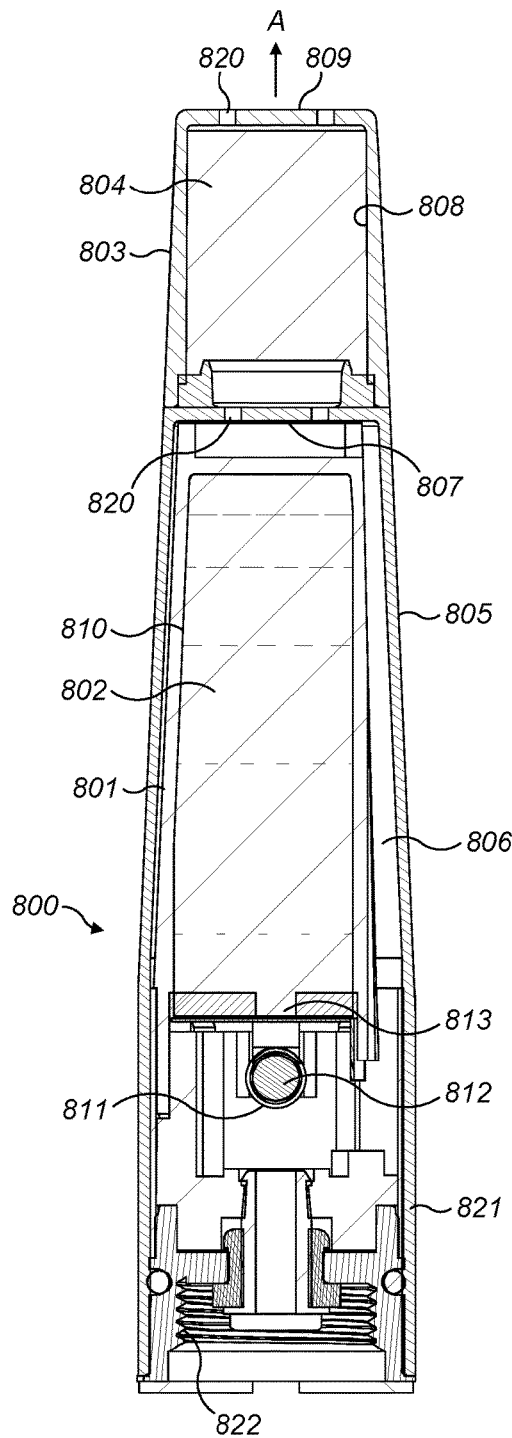
FIGS. 8a-8e show schematic longitudinal cross-sectional views of an example of a cartridge having a liquid container and an integral container for solid material and components thereof.
Figure 8B:
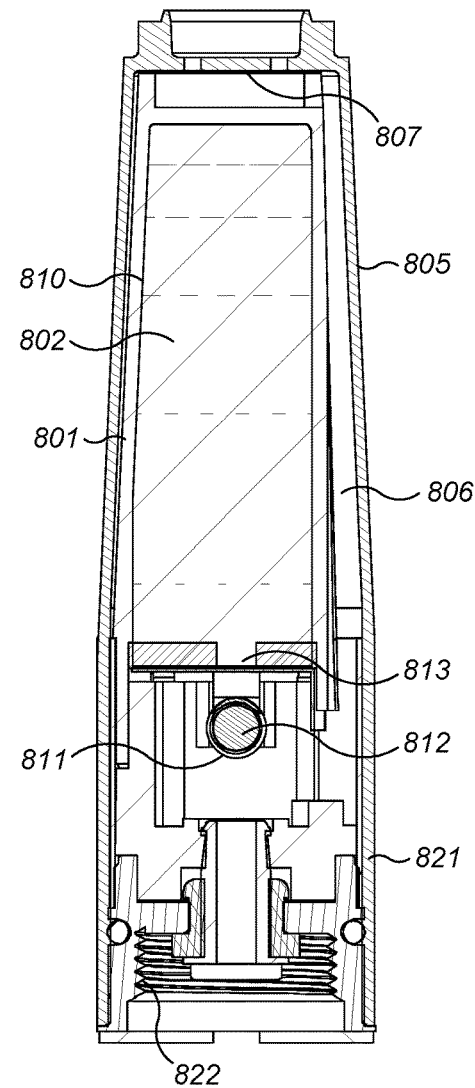
Figure 8E:
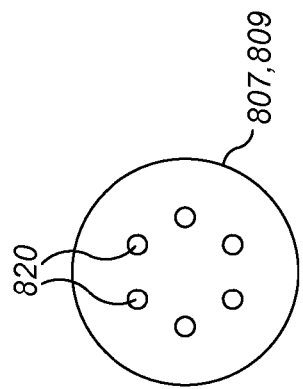
Figure 8D:
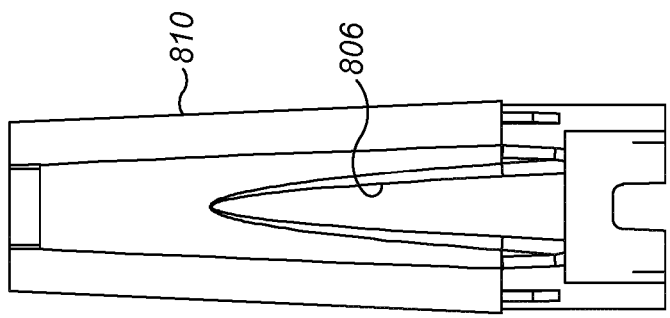
Figure 8C:
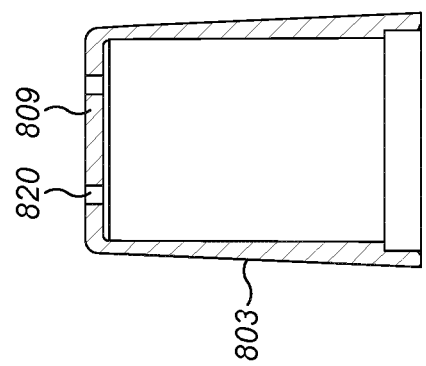

Referring now to FIGS. 8a-8e, there is shown a further example of a cartridge 800 having a liquid container 801 for containing liquid 802 and a receptacle or container 803 for material 804, which will typically be solid material 804. In this example, the liquid container 801 and the material container 803 are provided as one integral component by being formed initially of two parts, shown separately in FIGS. 8c and 8d, which are then assembled as shown in FIG. 8b in a substantially permanent fashion. The liquid container 801 and the material container 803 may be fixed to each other by for example friction welding, such as spin welding, ultrasonic welding, etc. The cartridge 800 is arranged so that as the liquid 802 is volatilized so as to produce an aerosol of liquid droplets or sufficiently heated to produce a vapor, at least some and in some embodiments all or substantially all of the aerosol or vapor passes through the material 804 to pick up flavor from the material 804.

Many aspects and features of the example of FIGS. 8a-8e are similar to the examples described above with reference to FIGS. 4 and 5 and a detailed description of those aspects and features will not be repeated here for the sake of brevity. Briefly, the liquid container 801 of the cartridge 800 has an outer shell 805 which defines a groove or channel 806 around the outside of the length of the inner liquid container part 810 and which extends from one end of the liquid container 801 to the other. In the example shown, this channel is provided by a groove 806 in the outer wall of the inner liquid container part 810, as can be seen most clearly in FIG. 8d. The cartridge 800 has a heater 811 for heating liquid and a wick 812 in thermal contact with the heater 811. The heater 811 may be for example an electrically resistive heater, a ceramic heater, etc. In this example, the heater 811 and the wick 812 are provided as a single unit. In this case, where the cartridge 800 includes a heater 811, such a cartridge is often referred to as a "cartomizer". The wick 812 is in contact with the liquid 802. As above, this may be achieved by for example the wick 812 being inserted through a through hole in the second end wall 813 of the inner liquid container part 810. Alternatively or additionally, the second end wall 813 may be a porous member which allows liquid to pass through from the inner liquid container part 810, and the wick 812 may be in contact with the porous second end wall 813. The second end wall 813 may be for example in the form of a porous ceramic disk. The wick 812 is generally absorbent and acts to draw in liquid 802 from the inner liquid container part 810 by capillary action. The wick 812 can be non-woven and may be for example a cotton or wool material or the like, or a synthetic material, including for example polyester, nylon, viscose, polypropylene or the like, or a ceramic material.

In use, the cartridge 800 is connected by the user to a battery section of an apparatus (which may for example be an apparatus 600 like that shown in FIGS. 6 and 7) to enable the liquid heater 811 to be powered. When the liquid heater 811 is powered (which may be instigated for example by the user operating a button 604 of the overall apparatus 600 or by a puff detector of the overall apparatus 600, as is known per se), liquid 802 drawn in from the inner liquid container part 810 by the wick 812 is heated by the heater 811 to volatilize or vaporise the liquid. As the user draws on a mouthpiece 603 of the overall apparatus 600, the vapor or aerosol passes into the channel 806 of the liquid container 801 and into the chamber 808 that contains the solid material 804. The vapor or aerosol picks up flavor from the material 804. In the case that the material 804 contains or includes nicotine, the vapor or aerosol also contains nicotine entrained from the material 804. The vapor or aerosol can then exit the cartridge 800 as shown by the arrow A. A one way valve (not shown) may be provided so that the vapor or aerosol can only exit the cartridge 800 and cannot back-flow to the heater 811 or the electronics of the apparatus as a whole.

The chamber 808 for the solid material 804 is closed off at the mouth end by an end wall 809 which is spaced from the end wall 807 of the liquid container 801. The end wall 809 of the chamber 808 may be provided by a separate retainer, for example an end wall 809 in the form of a disk which is inserted into the chamber 808 during manufacture. As an alternative, as in the example shown, the end wall 809 may be part of the material container 803. The end wall 809 may be formed of plastics or rubber or ceramic or the like and has one or more through holes 820 to allow aerosol or vapor to pass through the mouth end of the cartridge 800.

Similarly, the end wall 807 of the liquid container 801 may be provided by a separate retainer, for example an end wall 807 in the form of a disk which is fitted to the liquid container 801 during manufacture, or, as in the example shown, the end wall 807 may be part of the liquid container 801. The end wall 807 may be formed of plastics or rubber or ceramic or the like and has one or more through holes 820 to allow aerosol or vapor to pass into the chamber 808 which contains the solid material 804.

The end wall 807 of the liquid container 801 and the end wall 809 of the solid material chamber 808 assist in retaining the solid material 804 in position in the solid material chamber 808, both during transport of the cartridge 800 and during use of the cartridge 800.

Referring now to FIGS. 9a-9e, there is shown a further example of a cartridge 900 having a liquid container 901 for containing liquid 902 and a receptacle or container 903 for material 904, which will typically be solid material 904. Many aspects and features of the example of FIGS. 9a to 9e are similar to the example described above with reference to of FIGS. 8a-8e and a detailed description of those aspects and features will not be repeated here for the sake of brevity.

In this example, the liquid container 901 and the material container 903 are provided as separate parts, shown separately in FIGS. 9c and 9d. The liquid container 901 and the material container 903 may be connected or fixed to each other during manufacture, by for example clipping them together, by friction welding, such as spin welding, ultrasonic welding, etc. As an alternative, the liquid container 901 and the material container 903 may be connected or fixed to each other by the user during use, with the material container 903 being in the form of a removable end cap. In such a case, the user can easily replace one or other of the liquid container 901 and the material container 903 as required as the liquid 902 or solid material 904 as the case may be is consumed during use. The material container 903 may be fitted to the liquid container 903 by for example clips and/or as a friction fit. The cartridge 900 is again arranged so that as the liquid 902 is volatilized so as to produce an aerosol of liquid droplets or sufficiently heated to produce a vapor, at least some and in some embodiments all or substantially all of the aerosol or vapor passes through the material 904 to pick up flavor from the material 904.

The chamber 908 for the solid material 904 is closed off at the mouth end by an end wall 909. In the example shown the end wall 909 at the mouth end of the chamber 908 is provided by a separate disk which is inserted into the chamber 908 during manufacture. The end wall 909 may be formed of plastics or rubber or ceramic or the like and has one or more through holes 920 to allow aerosol or vapor to pass through the mouth end of the cartridge 900. As an alternative, the end wall 909 may be part of the material container 903, and similarly has one or more through holes to allow aerosol or vapor to pass through the mouth end of the cartridge 900 to be inhaled by a user. In a further alternative, the chamber 908 may have a second end wall or cap (not shown) having through holes, spaced from the end wall 909 at the mouth end. In this way, the chamber 908 for the solid material 904 can provide a complete unit that contains the solid material 904, which facilitates manufacture of the overall cartridge 900 and/or simplifies replacement of the chamber 908 by the user once the solid material 904 has been consumed.

Similarly, in the example shown, the end wall 907 of the liquid container 901 is provided by a separate disk which is fitted to the liquid container 901 during manufacture. The end wall 907 may be formed of plastics or rubber or ceramic or the like and has one or more through holes 920 to allow aerosol or vapor to pass into the chamber 908 which contains the solid material 904. As an alternative, the end wall 907 may be part of the liquid container 901, and similarly has one or more through holes to allow aerosol or vapor to pass through. Either way, the liquid container 901 can be a complete, sealed unit that contains the liquid 902, which facilitates manufacture of the overall cartridge 900 and/or simplifies replacement of the liquid container 901 by the user once the liquid 902 has been consumed.

In the example of FIG. 9a-9e, the material container or end cap 903 is a female connector, having an annular end wall 921 which fits over the end of the liquid container 901 in use. In FIGS. 10a-10e, there is shown another example cartridge 1000 having a liquid container 1001 for containing liquid 1002 and a receptacle or container 1003 for material 1004, which will typically be solid material 1004. The example of FIGS. 10a-10e is very similar to the example of FIGS. 9a-9e except that in this case, the material container or end cap 1003 is a male connector, having an annular end wall 1021 which fits within the end of the liquid container 1001 in use. FIGS. 10a-10e also show an example of the embodiment mentioned above in which the material container 1003 has a second end wall or cap 1009' having through holes, spaced from the end wall or disk 1009 at the mouth end, so that the chamber 1008 for the solid material 1004 provides a complete unit that contains the solid material 1004.

The examples shown in FIGS. 4, 5 and 8-10 are particularly suitable for use with so-called modular products, in which the cartomizer is fitted to a battery section of an overall apparatus (such as a battery section 601 of an apparatus 600 as shown in FIGS. 6 and 7), typically by a screw thread, a bayonet fitting or the like. The cartomizer as a whole is typically discarded after use and a new, replacement cartomizer used. As an alternative, it may be possible for the user to re-use the cartridge by refilling the liquid and/or replacing the solid material from time to time as necessary.

The examples shown in FIGS. 4, 5 and 8-10 may easily be adapted for use with other types of e-cigarette apparatus, which are known per se. There are for example so-called "look alike e-cigarette" or "cig-alike" devices which are generally small and have a form and appearance similar to a conventional cigarette. In such devices, the liquid container typically includes some wadding material, of for example cotton or the like, for holding the liquid. The cartridge or cartomizer in such known devices is typically disposable as a whole, but it may be possible to refill the liquid and/or replace the solid material in examples that use an embodiment of the present invention. As another example, there are so-called tank devices or personal vaporisers which generally have large liquid containers for holding relatively large volumes of liquid and also provide for advanced functions that allow users to control a number of aspects of the device.

As an alternative to any of the cartomizer arrangements discussed above, the heater for the liquid may be provided separately of the liquid and material containers. The heater may for example be provided as part of the battery section 601 of the overall apparatus 600 to which the cartridge is detachably fitted by the user in use.

In any of the examples described above in relation to FIGS. 4, 5 and 8-10, there may also be provided a heater for the solid material so as to "pre-heat" the solid material. This solid material heater may be provided as part of the cartridge or as part of the battery section of the apparatus to which the cartridge is fitted in use.

A number of other variations and alternatives to the examples described above are possible.

For example, in some cases it may be possible for the solid material to be located, exclusively or additionally, in the mouthpiece of the apparatus (e.g. the mouthpiece 603 of an apparatus 600 as described above) which with the cartridge described above is used.

As another example, the solid material may be omitted from the container, for example at the option of the user. This provides the user with more flexibility over the use of the cartridge as the user can use the cartridge as a classic "e-cigarette" device, only vaporising liquid and not having the vapor or aerosol pass over or through solid material, from time to time if they choose. This is particularly the case for the examples where the solid material in the solid material container is replaceable by the user.

In some examples, the outer shell 405, 505, etc. of the liquid container may extend beyond the heater 411 and wick 412 to form a skirt which in use fits around a part of the housing or battery section 601 of the apparatus 600 with which the cartridge 400, 500, 800, etc. is used. Such a skirt 821 is shown in particular for the example of FIGS. 8a-8e. These figures also show an example of the screw thread 822 in the cartridge 800 for fitting the cartridge 800 to the battery section 601 of the apparatus 600 as mentioned above.

It is described above that the channel through which aerosol/vapor flows from the liquid heater to the solid material is annular and completely surrounds the liquid container in some examples (e.g. the annular channel 406, 506 for the examples shown in FIGS. 4 and 5). In other examples, the channel is not annular and does not surround the liquid container 401,501,801, etc. For example, in some examples, such as that shown in FIGS. 8a to 8e, there may be a single, substantially tubular channel or groove extending from the liquid container to the solid material. As another example, there may be plural channels or grooves extending from the liquid container to the solid material, one or more of which may be substantially tubular. Where there are plural channels, it is possible for the channels to be filled with or contain or lead to materials having different properties. For example, one channel may be filled with or contain or lead to a material that imparts a first flavor to the vapor or aerosol, a second channel may be filled with or lead to a material that imparts a second flavor to the vapor or aerosol, etc.

In the examples above, the liquid container and the solid material/solid material container are arranged substantially in-line, along a longitudinal axis of the apparatus or cartridge. In other examples, the liquid container and the solid material/solid material container are arranged so as to at least partially overlap in the longitudinal direction of the apparatus or cartridge; in such examples, the liquid container and the solid material/solid material container may still be arranged generally in-line along the longitudinal axis of the apparatus or cartridge, or may be arranged side by side, or with one partially or completely inside the other. In yet other examples, the liquid container and the solid material/solid material container are arranged concentrically (either with the liquid container inside the solid material/solid material container or vice versa), and may be arranged to be entirely off-set with respect to each other along the longitudinal axis of the apparatus or cartridge, or overlapping, or one completely within the other.

As another specific example, the solid material/solid material container is placed in at least one channel between the heater and the outlet, the channel at least partially overlapping with the liquid container in the longitudinal axis of the apparatus or cartridge. In other words, the vapor or aerosol flow channel goes past the liquid container and the material is located somewhere within the channel.

The cartridge may comprise a cooler or heat exchanger, and/or the apparatus with which the cartridge 400,500, 800, etc. is used may comprise a cooler or heat exchanger. The material and the cooler in such an arrangement may be separate and spaced from each other. The cooler may be downstream of the liquid heater and upstream of the receptacle, the cooler or cooling zone being arranged to cool vaporised liquid to form an aerosol of liquid droplets which in use passes through material received in the receptacle. The cooler may be arranged in effect to act as a heat exchanger, allowing for recovery of heat from the vapor. The recovered heat can be used for example to pre-heat the material and/or to assist in heating the liquid As described in relation to the first set of examples above, the liquid can be a liquid that is volatilizable at reasonable temperatures, such as in the range of 100-300° C. or more particularly around 150-250° C., as that helps to keep down the power consumption of the apparatus with which the cartridge is used. Suitable materials include those conventionally used in e-cigarette devices, including for example propylene glycol and glycerol (also known as glycerine). Also as described in relation to the examples above, the solid material is a material that may be used to impart a flavor to the aerosol or vapor produced from the liquid as the aerosol or vapor passes through the material. The material may for example consist of or comprise tobacco. As the aerosol or vapor passes through and over the tobacco material, the hot aerosol or vapor entrains organic and other compounds or constituents from the tobacco material that lend tobacco its organoleptic properties, thus imparting the flavor to the aerosol or vapor as it passes to the mouthpiece. It will be understood however that materials other than tobacco may be used to impart different flavors to the aerosol or vapor stream. For example, flavorants could be included in the material or in the liquid.

In any of the examples described above, the apparatus controller controls operation of the apparatus as a whole. The controller for example may cause the or each heating element to be powered as and when required and switch off the or each heating element when heating is not required. Operation of the one or more heating elements may be controlled so that the liquid and/or material is heated to an optimum temperature. Particular considerations include ensuring that the material does not burn, ensuring that adequate vaporisation of the liquid is achieved, ensuring that the vaporised liquid or aerosol is at an appropriate temperature to liberate compounds from the material, and ensuring that the vapor or aerosol that reaches the user is at a comfortable and safe temperature. A puff detector, a device which is known per se, may be provided to signal to the controller when the one or more heating elements need to be energized. The apparatus may also have one or more filters for filtering the vapor or aerosol before it reaches the user, cooling arrangements for cooling the vapor or aerosol before it reaches the user, insulation internally of the apparatus to protect the user from the heat generated inside the housing, etc.

In use, and particularly in the case that the material 14, 214, etc. is tobacco, the tobacco, or at least the surface of the tobacco, can be heated to a temperature of between around 190° C. to 210° C. such as around 200° C., so as to ensure that an adequate or appropriate amount of the compounds are released from the tobacco. As described in more detail above, the material may be heated only by the hot vapor or aerosol that passes through the material or the material may also be pre-heated or dual-heated using for example a dedicated heater. In the case of pre-heating, the material, particularly in the case of tobacco, may be pre-heated to a temperature in the range of around 100 to 150° C. It will be appreciated however that other temperatures may be used. For example, the material, or at least the surface of the material, may be heated to a temperature above 210° C., such as up to around 230° C. or 240° C. or so and even as high as 290° C. or so. The amount of tobacco present may be for example in the range 50 to 300 mg or so. A most suitable value for the amount of tobacco may be for example in the range 50 to 150 mg, with 130 mg being a value that is currently found to be particularly suitable in some applications. In a typical example, the amount of tobacco that is heated per operation of the apparatus (i.e. per puff) may be in the corresponding range of around 8 to 50 mg.

In use, the liquid 10, 210, etc. may be heated to a temperature of between around 100-300° C. or more particularly around 150° C. to 250° C.

Suitable materials 14, etc. include materials that provide volatilized components upon heating, typically in the form of an aerosol. Suitable materials 14, etc. include any tobacco-containing material and may, for example, include one or more of tobacco per se, different varieties of tobacco, tobacco derivatives, expanded tobacco, reconstituted tobacco, ground tobacco, tobacco extract, homogenized tobacco or tobacco substitutes. In the case of tobacco, the material 14, etc. may be in the form of a rod of tobacco, a pod or plug of tobacco, loose tobacco, agglomerates, etc., and may be in relatively dry form or in relatively moist form for example. Suitable materials 14, etc. may include other, non-tobacco, products, which, depending on the product, may or may not contain nicotine.

In the particular case that the solid material is tobacco, the tobacco may be in the form of a plug of tobacco rod which is cut to length and placed into the receptacle or container for the solid material before the receptacle or container for the solid material is combined with the liquid container (whether the receptacle or container for the solid material is combined with the liquid container during manufacture or by the user in use).

In some examples, the receptacle or container for the solid material is transparent, so that the user can see the contents (i.e. the solid material) in use, which is appealing to some users. The tobacco rod may be formed using a transparent material as a wrapping material, again so that the user can see the tobacco. A particularly suitable material is Nature-Flex™, a biodegradable film made from renewable raw materials by Innovia Films Limited.

As used herein, the terms "flavor" and "flavorant" refer to materials which, where local regulations permit, may be used to create a desired taste or aroma in a product for adult consumers. They may include extracts (e.g., licorice, hydrangea, Japanese white bark magnolia leaf, chamomile, fenugreek, clove, menthol, Japanese mint, aniseed, cinnamon, herb, wintergreen, cherry, berry, peach, apple, Drambuie, bourbon, scotch, whiskey, spearmint, peppermint, lavender, cardamom, celery, cascarilla, nutmeg, sandalwood, bergamot, geranium, honey essence, rose oil, vanilla, lemon oil, orange oil, cassia, caraway, cognac, jasmine, ylang-ylang, sage, fennel, piment, ginger, anise, coriander, coffee, or a mint oil from any species of the genus Mentha), flavor enhancers, bitterness receptor site blockers, sensorial receptor site activators or stimulators, sugars and/or sugar substitutes (e.g., sucralose, acesulfame potassium, aspartame, saccharine, cyclamates, lactose, sucrose, glucose, fructose, sorbitol, or mannitol), and other additives such as charcoal, chlorophyll, minerals, botanicals, or breath freshening agents. They may be imitation, synthetic or natural ingredients or blends thereof. They may be in any suitable form, for example, oil, liquid, or powder.

In order to address various issues and advance the art, the entirety of this disclosure shows by way of illustration and example various embodiments in which the claimed invention may be practiced and which provide for a superior apparatus arranged to generate an inhalable medium. The advantages and features of the disclosure are of a representative sample of embodiments only, and are not exhaustive and/or exclusive. They are presented only to assist in understanding and teach the claimed and otherwise disclosed features. It is to be understood that advantages, embodiments, examples, functions, features, structures and/or other aspects of the disclosure are not to be considered limitations on the disclosure as defined by the claims or limitations on equivalents to the claims, and that other embodiments may be utilized and modifications may be made without departing from the scope and/or spirit of the disclosure. Various embodiments may suitably comprise, consist of, or consist in essence of, various combinations of the disclosed elements, components, features, parts, steps, means, etc. The disclosure may include other inventions not presently claimed, but which may be claimed in future.

The invention claimed is:

1. A cartridge for use with an apparatus for generating an inhalable medium, the cartridge comprising:
   a liquid container for holding a liquid;
   a receptacle for receiving a solid material; and
   a shell around the outside of the liquid container,
   wherein the shell and the liquid container define between them a channel, wherein the channel is in the form of a substantially tubular channel which does not completely surround the liquid container, and wherein the cartridge is arranged such that in use liquid exiting the liquid container can flow, in the form of at least one of a vapor or an aerosol, through the channel to the receptacle and through solid material received by the receptacle in use.

2. The cartridge according to claim 1, wherein the cartridge has plural channels defined between the liquid container and the shell.

3. The cartridge according to claim 1, wherein the liquid container is frustoconical.

4. The cartridge according to claim 1, comprising a heater associated with the liquid container for volatilizing a liquid held in the liquid container in use.

5. The cartridge according to claim 1, comprising a heater associated with the receptacle for heating the solid material received by the receptacle in use.

6. The cartridge according to claim 1, wherein the liquid container has one or more apertures to allow liquid to exit the liquid container.

7. The cartridge according to claim 1, comprising a wick for wicking liquid held in the liquid container in use out of the liquid container.

8. The cartridge according to claim 1, wherein the liquid container and the receptacle are provided as an integral component.

9. The cartridge according to claim 1, wherein the liquid container and the receptacle are provided as separate components which are detachably connected to each other.

10. The cartridge according to claim 1, wherein the receptacle has at least one retainer for retaining solid material within the receptacle in use.

11. The cartridge according to claim 1, wherein the receptacle contains the solid material.

12. The cartridge according to claim 11, wherein the solid material is or comprises tobacco.

13. The cartridge according to claim 1, wherein the liquid container holds the liquid.

14. A system comprising:
   the cartridge according to claim 1; and
   the apparatus for generating the inhalable medium, the apparatus having a battery section and a mouthpiece, the cartridge being connectable to the apparatus.

15. A method of generating an inhalable medium using a cartridge and an apparatus, wherein the apparatus comprises a battery section and a mouthpiece, and wherein the cartridge comprises a liquid container containing a liquid, a receptacle containing a solid material, and a shell around the outside of the liquid container, wherein the shell and the liquid container define between them a channel, the cartridge being connected to the apparatus, the channel being in the form of a substantially tubular channel which does not completely surround the liquid container, the method comprising:
   heating liquid drawn from the liquid container to vaporize the liquid;
   passing the vaporized liquid through the channel defined between the liquid container and the shell of the cartridge, into the receptacle containing the solid material and through the solid material so as to entrain at least flavor from the solid material to produce a flavored aerosol; and
   passing the flavored aerosol through the mouthpiece of the apparatus.

16. A liquid container for holding a liquid, the liquid container being for use with a receptacle for receiving a solid material to form a cartridge for use with an apparatus for generating an inhalable medium, the liquid container comprising:
   an inner container for holding the liquid;
   a shell around the outside of the liquid container; and
   a connector to enable the liquid container to be connected to the receptacle, wherein the shell and the liquid container define between them a channel, wherein the channel is in the form of a substantially tubular channel which does not completely surround the liquid container.

17. The liquid container according to claim 16, wherein the connector is in the form of an annular end wall that is receivable in or around the receptacle.

18. The liquid container according to claim 16, wherein the liquid container has plural of the channels defined between the inner container and the shell.

19. The liquid container according to claim 16, wherein the liquid container is frustoconical.

20. A method of forming a cartridge for use with an apparatus for generating an inhalable medium, the cartridge comprising a liquid container for holding a liquid, a receptacle for receiving a solid material, and a shell around the outside of the liquid container, wherein the shell and the liquid container define between them a channel, wherein the channel is in the form of a substantially tubular channel which does not completely surround the liquid container, the method comprising:
   loading the liquid container with the liquid;
   loading the receptacle with solid material; and
   connecting the liquid container and the receptacle together, such that in use liquid exiting the liquid container can flow, in the form of at least one of a vapor or an aerosol, through the channel to the receptacle and through solid material received by the receptacle in use.

21. The method according to claim 20, wherein the loading the receptacle with solid material comprises cutting a rod of the solid material to a desired length and placing the cut rod of solid material into the receptacle prior to connecting the liquid container and the receptacle together.

22. The method according to claim 20, wherein the solid material is wrapped in a transparent material.

23. The method according to claim 20, wherein the solid material is or comprises tobacco.

* * * * *